US011260109B2

(12) United States Patent
Yen

(10) Patent No.: US 11,260,109 B2
(45) Date of Patent: *Mar. 1, 2022

(54) ALBUMIN NANOPARTICLES TO AUGMENT STEM CELL FUNCTION IN VIVO

(71) Applicant: Richard C. K. Yen, Yorba Linda, CA (US)

(72) Inventor: Richard C. K. Yen, Yorba Linda, CA (US)

(*) Notice: Subject to any disclaimer, the term of this patent is extended or adjusted under 35 U.S.C. 154(b) by 156 days.

This patent is subject to a terminal disclaimer.

(21) Appl. No.: 15/233,779

(22) Filed: Aug. 10, 2016

(65) Prior Publication Data

US 2016/0375105 A1  Dec. 29, 2016
US 2017/0128545 A9  May 11, 2017

Related U.S. Application Data

(63) Continuation-in-part of application No. 13/560,727, filed on Jul. 27, 2012, now abandoned, and a continuation-in-part of application No. 14/226,544, filed on Mar. 26, 2014, now Pat. No. 9,629,931, which is a continuation-in-part of application No. 12/927,543, filed on Nov. 16, 2010, now Pat. No. 9,226,898, and a continuation-in-part of application No. 13/560,727, filed on Jul. 27, 2012, now abandoned, and a continuation-in-part of application No. 13/604,770, filed on Sep. 6, 2012, now Pat. No. 9,351,925, and a continuation-in-part of application No. 13/605,765, filed on Sep. 6, 2012, now Pat. No. 9,504,641, application No. 15/233,779, filed on Aug. 10, 2016, which is a continuation-in-part of application No. 14/925,506, filed on Oct. 28, 2015, now abandoned.

(60) Provisional application No. 61/853,041, filed on Mar. 27, 2013, provisional application No. 62/123,481, filed on Nov. 18, 2014, provisional application No. 62/122,854, filed on Oct. 29, 2014, provisional application No. 62/230,629, filed on Jun. 11, 2015.

(51) Int. Cl.
| A61K 38/38 | (2006.01) |
| A61K 38/36 | (2006.01) |
| A61K 9/00 | (2006.01) |
| A61K 9/10 | (2006.01) |
| A61K 9/16 | (2006.01) |
| A61K 9/51 | (2006.01) |
| A61K 35/545 | (2015.01) |

(52) U.S. Cl.
CPC ............ *A61K 38/38* (2013.01); *A61K 9/0019* (2013.01); *A61K 9/10* (2013.01); *A61K 9/1676* (2013.01); *A61K 35/545* (2013.01); *A61K 38/363* (2013.01)

(58) Field of Classification Search
None
See application file for complete search history.

(56) References Cited

U.S. PATENT DOCUMENTS

| 4,440,679 | A | 4/1984 | Fernandes et al. |
| 6,262,019 | B1 | 7/2001 | Keller et al. |
| 6,264,988 | B1 * | 7/2001 | Yen ...................... A61K 9/1676 424/489 |
| 6,916,795 | B1 | 7/2005 | Youssef |
| 7,625,878 | B2 | 12/2009 | Stella et al. |
| 9,114,127 | B2 | 8/2015 | Yen |
| 2002/0142046 | A1 | 10/2002 | Yen |
| 2011/0189299 | A1 | 8/2011 | Okubo et al. |

OTHER PUBLICATIONS

Teo, A.K.K., et al. 2010 Biochem J 428: 11-23. (Year: 2010).*
Berg-Foels, W.S.V. 2014 Tissue Engineering Part B 20(1): 28-39. (Year: 2014).*
Choi, J-S., et al. 2016 Curr Stem Cell Rep 2: 85-94. (Year: 2016).*
Dimmeler, S., et al. 2014 Nature Medicine 20(8): 814-821. (Year: 2014).*
Braun-Falco, O., et al. 2000 Disorders of Hemostasis. In: Dermatology. Springer, Berlin, Heidelberg: pp. 955-980. (Year: 2000).*
European Commission, "Commission Implementing Decision (Feb. 12, 2015)", EU orphan designation No. EU/3/15/1442, Feb. 12, 2015.
European Medicines Agency, "Public summary of opinion on orphan designation", EMA/COMP/55779/2015, Committee for Orphan Medicinal Products, Mar. 30, 2015.
World Health Organization, "Guidelines on viral inactivation and removal procedures intended to assure the viral safety of human blood plasma products", Annex 4, WHO Technical Report, Series No. 924, 2004.
Hosseini et al., "Study of the Heat-Treated Human Albumin Stabilization by Caprylate and Acetyltryptophanate", Dept. of R&D, Blood Research and Fractionation Co., Tehran, Iran, Iranian Biomedical Journal 6 (4): /35-140 (Oct. 2002).

(Continued)

*Primary Examiner* — Marsha Tsay
(74) *Attorney, Agent, or Firm* — David Guerra

(57) ABSTRACT

The present invention relates to a product and method of using albumin nanoparticles for augmenting the function or effectiveness of stem cells or precursor cells in vivo. An albumin nanoparticle suspension containing submicron albumin spheres is prepared, with the albumin spheres being capable of augmenting a function and effectiveness of stem cells or precursor cells in vivo. A predetermined amount of the albumin nanoparticle suspension is administered to a patient before or after an onset of at least one condition. The condition is one that can benefit from a healing effect of the stem cells or precursor cells. A function of the stem cells or precursor cells are augmented or improved by the albumin spheres to repair cellular or tissue damage, resulting in decreasing mortality or morbidity of the patient. The albumin spheres can be bound with fibrinogen molecules in vitro or in vivo.

8 Claims, 3 Drawing Sheets

(56) References Cited

OTHER PUBLICATIONS

Dr. Anrei Gudkov, Radiation Sickness Cures and Anti-Radiation Pills, http://nextbigfuture.com/2009/07/radiation-sickness-cures-and-anti.html, Jul. 20, 2009.
Smiley et al., "Fibrinogen stimulates macrophate chemokine secretion through toll-like receptor 4" J Immunol. Sep. 1, 2001; 167(5) abstract.
Perdomo et al., "Quinine-induced thrombocytopenia: drug-dependent GPIb/IX antibodies inhibit megakaryocyte and proplatelet production in vitro". Blood Jun. 2, 2011 vol. 117 No. 225975-5986.
Reiter et al., "Vitamin E and excessive bleeding" Ugeskr Laeger, Dec. 5, 2005; 167(49) (abstract).
Manjunatha, Antiboagulant proteins from snake venoms:structure, function and mechanism. Biochem J. (2006) 397, 377-387.
Blajchman,1996, "Evaluation of the in vivo Hemostatic Function of Human Platelets and Platelet Substitutes in a Thrombocytopenic Rabbit Model", In "Frozen Platelets and Platelet Substitutes in Transfusion Medicine" Mar. 7, 1996.
CDC, 2013, "Acute Radiation Syndrome Fact Sheet for Physicians", http://www.bt.cdc.gov/radiation/arsphysicianfactsheet asp, Page last reviewed: Oct. 22, 2013, Page last updated: Aug. 21, 2014.
CDC, 2014, "Questions and Answers on Ebola", CDC: Page last reviewed: Oct. 24, 2014, Page last updated: Oct. 24, 2014.
CDC, 2014, "Signs and Symptoms of Ebola", CDC: Page last reviewed: Oct. 18, 2014, Page last updated: Oct. 18, 2014.
Chen, 2014, "Edaravone Protects Human Peripheral Blood Lymphocytes from Gamma Irradiation-induced Apoptosis and DNA Damage", Cell Stress Chaperones, Sep. 3, 2014.
Gaugler, 2005, "A Unifying System: Does the Vascular Endothelium Have a Role to Play in Multi-organ Failure Following Radiation Exposure?", BJR Suppl 2005;27:100-5.
Higgins, 2014, "Ebola Facts: How Many Ebola Cases are Outside of West Africa?", By Andrew Higgins Oct. 17, 2014, New York Times.
Hutchinson, 2007, "Cytokine and Chemokine Expression in Humans Infected with Sudan Ebola Virus", Reprints or correspondence: Dr. Karen L. Hutchinson, Special Pathogens Branch, MS G-14, Centers for Disease Control and Prevention, 1600 Clifton Rd. NE, Atlanta, GA 30333 (kbh6@cdc.gov).
Kalamida, 2014, "Important Role of Autophagy in Endothelial Cell Response to Ionizing Radiation", PLoS ONE 9(7): e102408. doi: 10.1371/journal.pone.0102408.
Kelland, 2014, "More Cases of Ebola in Europe 'Unavoidable', WHO says", Reuters.com, Kate's Feed EMEA Health and Science Correspondent, Oct. 8, 2014.
King, 2014, "Ebola Virus Infection", http://emedicine.medscape.com/article/216288-overview.
Li, 2006, "The Preclinical and Clinical Trial of Platelet Substitute—Fibrinoplate", 4th Asian Pacific Congress On Thrombosis and Haemostasis, Suzhou, China, Sep. 23, 2006.
Rithidech, 2012, "Attenuation of Oxidative Damage and Inflammatory Responses by Apigenin Given to Mice After Iradiation", Mutat Res. Dec. 12, 2012;749(1-2):29-38. doi: 10.1016/j.mrgentox.2012.08 001. Epub Aug. 15, 2012.
Sanchez, 2004, "Analysis of Human Peripheral Blood Samples from Fatal and Nonfatal Cases of Ebola (Sudan) Hemorrhagic Fever: Cellular Responses, Virus Load, and Nitric Oxide Levels", J. Virol. Oct. 2004 vol. 78No. 19 10370-10377.
Sullican, 2003, "Ebola Virus Pathogenesis: Implications for Vaccines and Therapies", doi: 10.1128/JVI.77.18.9733-9737.2003, J. Virol. Sep. 2003 vol. 77 No. 18 9733-9737.
Sung, 2014, "Fibrinogen Coated Nanospheres Prevent Thrombocytopenia-related Bleeding", American Society of Hematologists annual meeting, Dec. 2014.
Winslow, 2013, "Oxygen: the Poison is in the Dose, Transfusion", Feb. 2013;53(2):424-37, doi: 10.1111/i.1537-2995.2012.03774.x. Epub Jul. 15, 2012.
Yang, 1998, "Distinct Cellular Interactions of Secreted and Transmembrane Ebola Virus Glycoproteins", Science 1998, Feb. 13:279 (5353):1034-7.
Yen, 1995, "A Novel Approach to Correcting the Bleeding Associated with Thrombocytopenia", Presented to American Association of Blood Banks: 48th annual meeting, Nov. 11-15, 1995.
Kutler et al., Annu Rev Med; 2009, 60:193-206.
Yasukochi et al., "Radiation-induced skin ulcer and rib fractures following percutaneous coronary internetion (PCI): A case of right back skin ulcer and adjacent rib fracture after single PCI", J. Dermatol,Mar. 20, 2015, doi: 10.1111/1346-8138.12839.
Shope et al., "Radiation-induced Skin Injuries from Fluoroscopy", RadioGraphy 1996, 16:1195-1199.
Xiao We Mao et al., "Effects of Fibrinoplate-S in a Radiated Mice Model", an abstract at the Radiation Research Society Annual Meeting held in Weston, FL, Sep. 19-22, 2015.
Nauth et al., "Stem Cells for the Repair and Regeneration of Bone" published in Indian J Orthop. Jan.-Feb. 2012; 46(1): 19-21.

* cited by examiner

ALBUMIN NANOPARTICLES TO AUGMENT STEM CELL FUNCTION IN VIVO

CROSS-REFERENCE TO RELATED APPLICATION

The present application claims priority under 35 U.S.C. 119(e) to U.S. provisional patent application No. 62/230,629 filed Jun. 11, 2015, which is incorporated herein by reference in its entirety This application claims the benefit of priority of and is a Continuation-In-Part under 35 U.S.C. § 120 based upon co-pending U.S. patent application Ser. No. 13/560,727, filed on Jul. 27, 2012, U.S. patent application Ser. No. 14/226,544, filed on Mar. 26, 2014, and U.S. patent application Ser. No. 14/925,506. The entire disclosures of the prior applications are incorporated herein by reference.

STATEMENT REGARDING PRIOR DISCLOSURES BY THE INVENTOR OR A JOINT INVENTOR

The following disclosures are submitted under 35 U.S.C. 102(b)(1)(B):

A "grace period disclosure" was published on Sep. 19-22, 2015 by way of an abstract at the Radiation Research Society Annual Meeting held in Weston, Fla. This publication was entitle "Effects of Fibrinoplate-S in a Radiated Mice Model". The applicant is a co-author of this publication. This Radiation Research Society Annual Meeting obtained the subject matter indirectly from the applicant not more than one year before the effective filing date of the claimed invention.

A "grace period disclosure" was published on Oct. 28, 2015 by the Basic Sciences Department School of Medicine at Loma Linda University. This publication was entitled "Fibrinoplate-S for the Treatment of Radiation-induced Skin Damage". Loma Linda University obtained the subject matter indirectly from the applicant not more than one year before the effective filing date of the claimed invention.

BACKGROUND OF THE INVENTION

Field of the Invention

The present invention relates to using protein nanoparticles to augment the function or effectiveness of stem cells or precursor cells in vivo, including their production, mobilization and effectiveness in regenerative medicine and biology.

Description of the Prior Art

Stem cells are known to be the precursors of new cells formation or tissue regeneration. The field of studying stem cells in order to encourage their conversion into mature cells that can perform specific functions in the body is called regenerative biology or regenerative medicine. Some tissues and organs are more capable of regeneration after injury, e.g. the liver. It has been known now that the new liver cells are not necessarily all derived from already-formed mature liver cells that were there in the liver before the injury, but that stem cells from their sources in the body, having migrated there from the rest of the body, become "informed" of their location and then those stem cells become liver cells. Other cells or tissues are more difficult to regenerate, e.g. nerve cells. There is a dire need for methods to encourage stem cells production in vivo which can regenerate at specific sites into new and functional cells, e.g. functional nerve cells in patients with major spinal injury. Alternatively, even if there is no net gain in the production of stem cells, but they are mobilized from the site of production to the site where they are needed or do maximum benefit, the patient will benefit.

Numerous investigators have demonstrated that certain biological molecules, such as those produced by recombinant DNA methods (e.g. Neupogen, thrombopoietin, and erythropoietin) or naturally derived molecules can increase the production of white cells or platelets or red blood cells. However, these molecules all require the presence of a sufficient number of competent stem cells in the body and several days if not weeks for the stem cells to develop into mature and functional cells. There is a need for a product and a method to provide quicker and more effective remedies to patients who can be help by improved stem cell functions in a short time period.

In addition, small molecules can mimic the effect of such large biological products in stimulating the formation of mature blood cells. The small mimetic molecules can be peptide in nature (e.g. Romiplostim) or non-peptide in structure (e.g. Eltrombopag). But they have long-term problems such as "thrombosis, increased bone marrow reticulin, rebound worsening of thrombocytopenia upon discontinuation, and increased blast formation" (Kuter et al, Annu Rev Med; 2009, 60:193-206).

Efficacy of new molecules or compounds that can affect stem cell function is typically assessed by the resulting increase in cell concentrations in the blood. In the case of blood cells, they can easily be measured by the machines in the clinical laboratory. However, most stem cells regenerate into tissues that cannot be measured by the standard machines. Indeed, the effect of any method to augment the function of stem cells for regeneration of solid tissues or organs is difficult to measure. In addition, the improved functionality of stem cells may not necessarily be expressed in term of the number or the concentration of new progeny cells produced, it can be expressed in terms of a more robust or faster healing, or other measures. In order not to be restricted to "increase in cell number" we prefer to use the term augmentation. By augmentation in this disclosure, we mean any of the following: (a) increase in production in the number of stem cells capable of developing into functional mature cells; (b) increase in the speed with which stem cells mature; (c) increase in the functionality of either the stem cells or the mature cells in doing their job in the body; (d) decrease in the destruction of stem cells or their mature cells; (e) mobilization of stem cells from the site of production to the site of transformation where the stem cells become beneficial to the host; (f) any other mechanism leading to a decrease in the morbidity and mortality of the patient in a process in which stem cells are needed to restore health. Such methods are lacking in the prior arts.

For exemplary purposes, a model of burn to test the ability of stem cells to resolve the wound has been chosen. The model will consider the speedy resolution of a burn area to be a reflection of the augmentation of stem cell function regardless of its precise mechanism. Burn is a difficult topic for study. There are many reasons for the difficulties: (a) the degree of burn, particularly thermal burn, can vary from first degree which is superficial, to third degree which is very deep; (b) the size and the location of the burn affect not only the healing process but also the death rate—when the size is small it can be treated easily, whereas a large area burn or in critical locations in the body, it can be fatal; (c) each patient from the same incident will not have the same pattern of burns and therefore there is no standard "control" cases to evaluate if a particular method is better than another.

At the present time, burn patients are treated with pain medication, fluid support, nutritional support, and transfusion of plasma, platelet, red cells, anti-anxiety, anti-infection and anti-stomach-acid agents. Skin grafts are often needed when the patient is stabilized. There are no proven methods to stabilize the vasculature to decrease or stop leaky vessels in order to control extravasation of blood components from the intravascular compartment to the extravascular compartment, or to promote healing at the early stage of the body's response to the injury. Therefore there is need also for an evaluation method which is easy to conduct in the laboratory, is reliable, and which can predict the efficacy of stem cell augmentation in the treatment for a variety of diseases including burn in the clinical setting.

Therefore, a need exists for new and improved albumin nanoparticles that can be used for augmenting the function or effectiveness of stem cells or precursor cells in vivo, including their production, mobilization and effectiveness in regenerative medicine and biology. In this regard, the present invention substantially fulfills this need. In this respect, the albumin nanoparticles according to the present invention substantially departs from the conventional concepts and designs of the prior art, and in doing so provide an apparatus primarily developed for the purpose of augmenting the function or effectiveness of stem cells or precursor cells in vivo, including their production, mobilization and effectiveness in regenerative medicine and biology.

BRIEF SUMMARY OF THE INVENTION

In view of the foregoing disadvantages inherent in the prior art, the present invention provides improved albumin nanoparticles and method of augmenting the function or effectiveness of stem cells or precursor cells in vivo, including their production, mobilization and effectiveness in regenerative medicine and biology, and overcomes the above-mentioned disadvantages and drawbacks of the prior art. As such, the general purpose of the present invention, which will be described subsequently in greater detail, is to provide new and improved albumin nanoparticles and method which has all the advantages of the prior art mentioned heretofore and many novel features that result in augmenting the function or effectiveness of stem cells or precursor cells in vivo, including their production, mobilization and effectiveness in regenerative medicine and biology which is not anticipated, rendered obvious, suggested, or even implied by the prior art, either alone or in any combination thereof.

The present invention is a product and a method to augment the function or effectiveness of stem cells in vivo. It is also a laboratory method to evaluate the effectiveness of such augmentation towards an improvement in healing. The product is a suspension of protein nanometer-sized particles which will be administered intravenously to a patient who can be helped by improved stem cell function. An exemplary model of evaluation comprises of the creation of a non-lethal, non-painful and standardized burn on the skin, the administration of the to-be-evaluated stem-cell-augmenting agent, and the collection of efficacy data soon after administration of the stem-cell-augmentation agent.

To attain this, the present invention essentially comprises a product and method of using albumin nanoparticles for augmenting the function or effectiveness of stem cells or precursor cells in vivo. An albumin nanoparticle suspension containing submicron albumin spheres is prepared, with the albumin spheres being capable of augmenting a function and effectiveness of stem cells or precursor cells in vivo. A predetermined amount of the albumin nanoparticle suspension is administered to a patient before or after an onset of at least one condition. The condition is one that can benefit from a healing effect of the stem cells or precursor cells. A function of the stem cells or precursor cells are augmented or improved by the albumin spheres to repair cellular or tissue damage, resulting in decreasing mortality or morbidity of the patient. The albumin spheres can be bound with fibrinogen molecules in vitro or in vivo.

The patient is non-thrombocytopenic or thrombocytopenic.

There has thus been outlined, rather broadly, the more important features of the invention in order that the detailed description thereof that follows may be better understood and in order that the present contribution to the art may be better appreciated.

The invention may also include the stabilizing of blood vessels by attachment of the albumin spheres on appropriate receptors on an endothelium of the blood vessels.

The invention in addition or optionally may include the activating against extravasation of blood components from an intravascular compartment to an extravascular compartment, so that there is less free hemoglobin in the extravascular compartment.

Still in addition or optionally the invention may include the stimulating a conversion of the stem cells or precursor cells to mature cells.

There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide new and improved protein nanoparticles to augment the function or effectiveness of stem cells or precursor cells in vivo that has all of the advantages of the prior art and none of the disadvantages.

It is another object of the present invention to provide new and improved protein nanoparticles that may be easily and efficiently manufactured and marketed.

An even further object of the present invention is to provide new and improved protein nanoparticles that have a low cost of manufacture with regard to both materials and labor, and which accordingly is then susceptible of low prices of sale to the consuming public, thereby making such protein nanoparticles economically available to the buying public.

Still another object of the present invention is to provide new protein nanoparticles that provides in the products and methods of the prior art some of the advantages thereof, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE INVENTION

Figure 1:
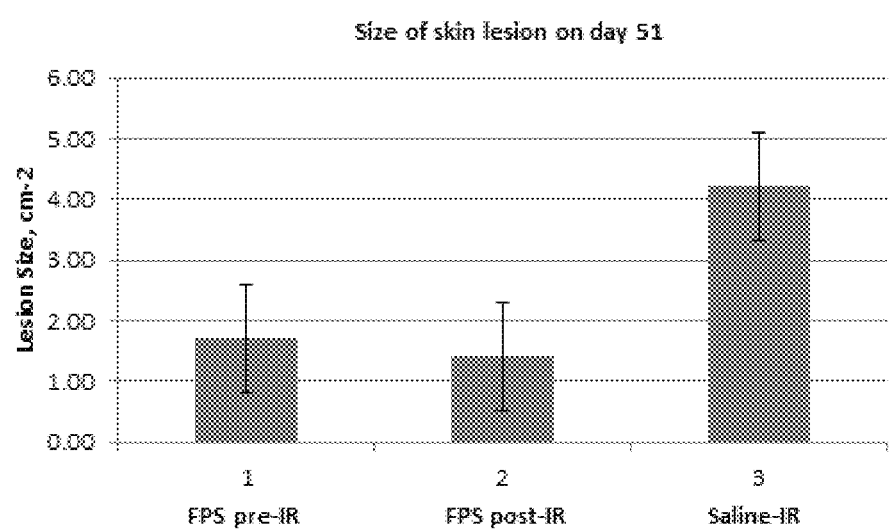
FIG. 1 is a graphical view of the size of lesions in control and treatment groups.

Stem cells are known to be the precursors of new cells formation or tissue regeneration. The field of studying stem cells in order to encourage their conversion into mature cells that can perform specific functions in the body is called regenerative biology or regenerative medicine. Some tissues and organs are more capable of regeneration after injury, e.g. the liver. It has been known now that the new liver cells that are formed in vivo after a liver injury are not necessarily derived from the division of already-formed mature liver cells that were there in the liver before the injury, but that stem cells from their sources in the body, having migrated there from the rest of the body, become "informed" of their location and then those stem cells become liver cells. Other cells or tissues are more difficult to regenerate, e.g. nerve cells. There is a dire need for methods to encourage stem cells production in vivo which can regenerate at specific sites into new and functional cells, e.g. functional nerve cells in patients with major spinal injury. Alternatively, even if there is no net gain in the production of stem cells, but they are mobilized from the site of production to the site where they are needed or do maximum benefit, the patient will benefit.

Stem cells are called "stem cells" because they are like the stem of a tree (with one main stem or trunk) but from it there can be derived many branches (different types of functional or mature cells, depending on the kind of stimuli that the stem cells get, informing them by biochemical signals what kind of more-specialized cells to become.) Sometimes stem cells are called bone marrow cells, immature cells, or precursor cells. Depending on how "primitive" they are, they can be toti-potential, which means that they can become any kind of mature cells, depending on the kind of signal they obtain from their environment, such as those stem cells in an embryo which will eventually develop into all the organs and tissues that a new-born baby will have. Sometimes, stem cells are called pluro-potential, if they are believed to be able to develop into a plurality of cells (and not "all kinds of cells"). A lot of research has gone into signaling stem cells in vitro so that they can grow into specific tissues which may be helpful for later transplant into patients. There is little inroad in encouraging stem cells to become useful tissues in vivo, except the few cases in the generation of blood cells as mentioned in the prior art.

The present invention indicates that the administration of nanoparticles can augment the function of stem cells related to the hematopoietic system. However, the data suggest that other stem cells are also stimulated, or become increase in number in the blood, such as those that will eventually give rise to muscles, connective tissues, connective cells, and skin cells which are all involved in wound healing.

The effect of stem cell stimulation can easily be seen in patients who need certain blood cells. Patients who lack sufficient red cells, or white cells, or platelets in their blood can benefit from stem cell stimulation to result in a restoration of the normal concentration of blood cells. Numerous investigators have demonstrated that certain biological molecules, such as those produced by recombinant DNA methods (e.g. Neupogen, thrombopoietin, and erythropoietin) or naturally derived molecules can increase the production of white cells or platelets or red blood cells. However, these molecules all require the presence of a sufficient number of competent stem cells in the bone marrow and will need several days if not weeks for the stem cells to develop into mature and functional cells. The present invention is to remedy this slow-response and provides a product and a method to result in a quicker and more effective remedy to patients who can be helped by improved stem cell functions, not restricted to low blood cells counts but in all cases where stem cell functions are needed for healing.

Efficacy of new products or compounds that can affect stem cell function is typically assessed by the resulting increase in cell concentrations, e.g. from the increase in the concentration of red blood cells, white blood cells or platelets in the blood. In the case of blood cells, they can easily be measured by the machines in the clinical laboratory. However, most stem cells regenerate into tissues that cannot be measured by the standard machines. Indeed, the effect of any method to augment the function of stem cells for regeneration of solid tissues or organs is difficult to measure. In addition, the improved functionality of stem cells may not necessarily be expressed in term of the number or the concentration of the progeny cells produced, it can be expressed in terms of a more robust or faster healing, or in other measures. In order not to be restricted to "increase in cell number" we prefer to use the term augmentation of stem cell function. By augmentation in this disclosure, we mean any of the following or a combination of these mechanisms: (a) increase in production in the number of stem cells capable of developing into functional mature cells; (b) increase in the speed with which stem cells mature; (c) increase in the functionality of either the stem cells or the mature cells in doing their job in the body; (d) decrease in the destruction of stem cells or their mature cells; (e) mobilization of stem cells from the site of production to the site of transformation where the stem cells become more mature cells with functions beneficial to the host; (f) any other mechanism leading to a decrease in the morbidity and mortality of the patient in a process in which stem cells are needed to restore health. This disclosure intends to describe not only the product and how it can be administered, but also a model with which to assess how well the product performs as well as the method of administration.

We choose to describe here a model of radiation-induced burn. We believe it applies to thermal burn also because the body's reaction is similar in both cases. In this disclosure, the term "burn" is used to mean (a) thermal burn, (b) cold-temperature-induced burn, or (c) radiation-induced burn. The context will reveal which burn we mean and we do not exclude the possibility of a combination of burns, such as can be experienced by workers in the nuclear industry where a fire can destroy structures leading to a worker being exposed to both thermal burn and radiation-induced burn. Regarding thermal burns, there are millions of people in the world who suffer from burn, such as in the kitchen or in car accidents. Yet it is difficult to evaluate new methods that are designed to decrease the morbidity and mortality after a burn incident. There are many reasons for the difficulties: (a) the degree of burn can vary from a first degree burn which is superficial, to a third degree burn which is very deep; (b) the morbidity and mortality rate depend on the size and the location of the burn on the body and whether there are additional co-morbidities, such a trauma or pre-existing medical conditions; (c) patients from the same incident will not have the same pattern of burns and therefore there is no standardized "control" cases to evaluate if a particular method is better than another; (d) it may not be ethical to withhold treatment (to set up a control case for comparison) just for the sake of evaluating whether a new method of burn-treatment is better than the standard method. However, regardless of the difficulties, long term healing of a burn will require the function of stem cells to repair the damage done to the skin and the deep tissues. Therefore, we believe this model of burn is a good reflection of the augmentation of stem cell function, as shown in the following experiments.

At the present time, burn patients are treated with pain medication, fluid support, and nutritional support. They need an abundance of blood components: plasma, platelets, red cells are often transfused, plus anti-infection, anti-anxiety, anti-stomach-acid agents. Skin grafts are often needed when the patient is stabilized. It is possible that the product of this invention works by stabilizing the blood vessels or the vasculature, or by decreasing or stopping the leakiness of blood vessels, or by decreasing the extravasation of blood components from the intravascular compartment to the extravascular compartment. We intend to disclose here evidence that the product and method of the present invention work at least partially through the augmentation of stem cell functions.

The present model of evaluation has many advantages. It is a method to create a standardized radiation-induced burn injury which is not painful, not lethal and easy to measure (by using a ruler to measure the diameter of the lesion on the skin that had been irradiated.) The number of animals needed is small, less than ten per group.

This method can also be used to show whether administration of the stem-cell-augmentor before the injury (prophylactically) is better, the same, or less effective than treatment after the injury (therapeutic approach.) One example of the importance of pre-treatment may be first responders who need to go inside a damaged nuclear energy facility, knowing that highly radioactive material may fall on them despite the best effect to avoid contact with such material. Likewise, fire-fighters may need to go into a fire where some can expect to become burned severely. Significantly, the treatment method being evaluated under this model is highly effective even when administered days after the onset of injury.

Again, the present invention includes a laboratory method to evaluate the effectiveness of any agent that can augment the function of stem cells, including the function to heal a burn long-term, which comprises of (a) the creation of a non-painful, non-lethal and yet standardized burn, (b) the administration of the stem-cell-augmentor to the burn patient and (c) the collection of efficacy (healing) data soon after the creation of the burn. The method is demonstratively useful for application of the agent to treat burn in the laboratory as well as in the clinical setting for patients who suffer from unintended burn, whether the burn is due to thermal burn, extremely-cold burn, or radiation burn.

Thermal burn will include all the typical burns involving heat or a fire, regardless of the source, such as from a kitchen fire or from a burning automobile. Extreme-cold burn will include the burn caused by someone touching extremely cold objects, such as dry-ice; or someone suffering from frost-bite. Radiation burn include radiation-induced skin injury or radiation ulcer, which occurred among victims of the Chernobyl accident and can occur among doctors, workers and patients exposed to high doses of ionizing and non-ionizing irradiation during radiological procedures, such as percutaneous coronary procedures, which uses fluoroscopy.

One stem cell augmentation method disclosed here comprises the intravenous administration of protein nanoparticles before or after the onset of the injury such as a burn, where the nanoparticles have the capacity to (a) improve or increase the function of cells to repair any cellular or tissue damage, (b) and/or directly stabilize the blood vessels by the attachment of the nanoparticles on the appropriate receptors on the endothelium of the blood vessels, (c) and/or by actions against extravasation of blood components from the intravascular compartment to the extravascular compartment, so that there is less free hemoglobin in the extravascular compartment, leading to improved morbidity and mortality of the patient.

All of the above effects can occur in patients who are non-thrombocytopenic (normal platelet count) as well as those that are thrombocytopenia (down to 3% of the normal platelet count) and can occur in an environment of platelet dysfunction (e.g. the endogenous platelets have been inhibited by medications such as aspirin, or by other treatments such as anti-platelet antibodies, or modified antibodies).

The evaluation-method testing this treatment-method is easy to use, and can show statistically-significant differences between the control group and any of the treatment groups in a short time. This evaluation-method allows the introduction to the clinical setting new treatment-methods which can readily be shown to be superior to the standard or conventional methods to stimulate the maturation of stem cells.

Description of One Particular Type of Burn

Radiation Skin Injury (RSI) is also known as radiation-induced skin injury, or radiation-induced skin ulcer. RSI is caused by close contact of the skin with a radiation source, such as the ionizing radiation material stored in the nuclear energy production plants. However, civilians outside the nuclear industry can also suffer from RSI, e.g. physicians and workers in the field of internventional radiology where fluorecopically-guided procedures are common. Many patients are also not conselled on the risk of radiation-induced injury probably because physicians are not in high alert that this can happen to the patient. Also the skin lesions develop typically after the patient has left the hospital after being seen or treated by the radiologist. In one report, the patient had refractory and severely painful skin ulcer on the right back after only one percutaneous coronary intervention (PCI) treatment because of the high and repeated doses used in that single procedure ("Radiation-induced skin ulcer and rib fractures following percutaneous coronary internetion (PCI): A case of right back skin ulcer and adjacent rib fracture after single PCI" Yasukochi, et al, J. Dermatol, 2015 Mar. 20, doi: 10.1111/1346-8138.12839).

The symptoms typically start after a variety of interventional procedures that require extended periods of flurorscopy compared with those of typical diagnostic procedures which use divided smaller doses over a longer period. The injury can range in severity from erythema to moist desquamation to tissue necrosis requiring skin grafting. Photographs of such injuries can be found in "Radiation-induced Skin Injuries from Fluoroscopy", Shope, et al, RadioGraphy 1996, 16:1195-1199.

In a public health advisory sent to the radiological community on Sep. 15, 1995, the FDA recommended that an absorbed dose of 1 Gy (100 rad) be considered as threshold for potential injury to the exposed person ("Important information for physicians and other healthcare professionals: recording information in the patient's medical record that identifies the potential for serious x-ray-induced skin injuries following fluoroscopically guided procedures" FDA, 1995).

RSI should not be confused with ultraviolet B-induced sun-burn which is superficial skin injury, even though some authors also call such sun-burns "radiation skin injury."

From the above discussion the reader should understand that RSI is a clinical condition even though the present invention comprises the creation of a radiation-induced ulcer in the laboratory as a model or condition where a new therapy for stem-cell augmentation can be evaluated.

Although the skin ulcer has been created in the present disclosure through a radiation source, it can be readily noted that burn can be created in the laboratory or under clinical conditions by extreme cold such as by close or direct contact of the skin with dry ice; or by a thermal burn.

EXPERIMENTS

Experiment One

An easy and painless burn model that can allow quantification of the effectiveness of a new stem-cell augmentation therapy. The data has been partially published in an abstract at the Radiation Research Society Annual Meeting held in Weston, Fla., Sep. 19-22, 2015; the title is "Effects of Fibrinoplate-S in a Radiated Mice Model" (Xiao Wen Mao et al. 2015).
Purpose:
Creation of a burn model capable of evaluating new stem-cell augmentation/burn-treatment therapies and the demonstration that at least one such stem-cell augmentation/burn-treatment method is effective in decreasing the damage done by the burn.
Experimental Design:
The design of this pilot study aims at collection of information that can support conducting a more complete study. The ultimate objective is to (a) set up a radiation-induced ulcer model; (b) evaluate the effect of an artificial platelet suspension (Fibrinoplate-S, FPS, also known as fibrinogen-coated albumin spheres) as the stem-cell augmentation agent. In this small pilot study Sprague Dawley rats will be treated with saline or saline plus 30 (or lower) Gy of gamma radiation, carrier vehicle (albumin solution at 8 mg per ml), carrier plus 30 Gy, FPS 8 mg/kg, FPS plus 30 Gy. Radiation will be delivered to one hind leg. The treatment includes the optimum concentration of FPS (8 mg/kg) given once a day for one to three (or fewer) days before radiation exposure to 30 Gy gamma rays or the same one-to-three doses given post-irradiation. The study endpoint will be acute skin toxicity including ulcer formation. The rats will be euthanized at 30 days post irradiation, or later. The expectation is that the FPS-treated animals will have decreased skin toxicity (transient erythema, dry or moist desquamation, thinning of the dermal tissue, dermal atrophy and necrosis) than the non-treated irradiated rat.

The follow-up studies will include the administration of anti-platelet antibodies such as anti-CD41 to inactivate endogenous platelets, which should increase the size of the ulcer and other radiation-induced damage by the same dose of radiation; or by even a lower dose of irradiation. The present invention expects that administration of FPS will improve the condition of the irradiated subject compared to the control treatment on similarly irradiated subjects.

This experiment is an important one because radiation-induced skin injury remains a significant problem. This injury, often referred to as radiation dermatitis, occurs in about 95% of patients receiving radiation therapy for cancer, and ranges in severity from mild erythema to moist desquamation and ulceration. Currently, there is no effective treatment to prevent or mitigate radiation skin injury.

A product like FPS, a synthetic platelet preparation, has distinct advantages. It has no immune reaction when given to anyone and has a shelf-life of at least 24 months when stored in room temperature without shaking or agitation. These features make it a very useful agent for reducing skin lesion from radiation therapy or national disasters such as terrorist act. This experiment is to determine whether the FPS will decrease the radiation-induced skin toxicity.

FPS (with a common name of fibrinogen-coated albumin spheres, FAS) has been shown not to affect blood cell concentrations when mixed with blood, nor blood chemistry (after correction for dilution with a volume of the FPS suspension.) The spheres in FPS only form co-aggregates with platelets when platelet-activating agents are added to the mixture.

This intention will disclose evidence that although FAS does not activate or actively interact with mature blood cells, it can have a positive interaction with immature blood cells or their precursors. In particular, stem cells of the white blood cell lineage are positively affected. There is also evidence FAS improves the healing process involving stem cells and their progeny cells which are not the "standard blood cells" (i.e. not red blood cells, not white blood cells, not platelets.)

Direct microscopic observation of the small blood vessels in a live mouse shows that FAS not only circulate near the endothelium of the blood vessels as expected, they can attach to the healthy blood vessels (which are not known to contain wounds or injuries.) The attachment starts within 10 minutes of the intravenous administration of FAS and lasts for 36 hours. Thereafter, the spheres are no longer observed on the inner surface of the blood vessels.

It has been observed by specialists (personal communication) that endothelial cells are involved in the formation of platelets from megakaryocytes in the bone marrow. Conventional wisdom would state that megakaryocytes would "bug off" platelets when they become mature. However, such a process does not occur randomly; it occurs in conjunction with endothelial cells. Therefore attachment of FAS onto the endothelium in the blood vessel in the ear of a live mouse suggests that the spheres may attach also to the endothelial cells inside the bone marrow, leading to positive reactions among stem cells there, resulting in lower morbidity of the patient.

The animals for the experiments will be purchased and allowed to acclimate for one week prior to random assignment to the 5 study groups. Control animals will be placed in similar boxes for an average time period to match the exposed animals. On the day of radiation exposure all rats will be weighed. The FPS is given 8 mg/kg of body weight. The rats are expected to be in the 25-30 gram range, or larger. Twenty-four hours post irradiation the animals in the non-treated control group will be given 60 ul of sterile saline through a tail vein injection. Control groups will receive saline or saline+30 Gy of gamma rays. Test group rats will receive 30 Gy gamma irradiation and 2-3 days before or after irradiation, the rats will be given 60 ul of the carrier for FPS which is albumin solution or FPS (depending on their weight–8 mg/kg stock is to be diluted to 4 mg/ml to provide adequate volume for injection) through the tail vein once per day for 2 or 3 days. The animals will be returned to their respective cages and closely monitored.

The mice are expected to have effects from the radiation, however the mice will not be allowed to suffer needlessly, if they loss 20% of their body weight in 3 consecutive weight measurements (days) they will be considered lethally affected by the radiation and will be euthanized with 100% $CO_2$ asphyxiation. The number of such affected/euthanized animals will be noted; if none is noted, that would mean the dose of irradiation has been safely administered to the skin of the animals. All the animals used in this experiment will be euthanized before the two-month time point following radiation exposure. The only distress the animals will experience is the irradiation procedure itself; intravenous administration of fluids or FPS does not cause undue pain to the animals.

In terms of the study groups and the controls; Table 1 provides the complete list. All groups have ideally 10 animals. A smaller number of animals per group is allowed if the effectiveness of stem-cell augmentation is obvious. However, the essential 5 groups are 1.1, 1.3, 2.2, 4.1 and 4.2.

TABLE 1

| Group No. | Group | Number of animals |
|---|---|---|
| 1.1. | Control-non-radiation + saline | 10 |
| 1.2. | Non-radiation + FPS (before radiation schedule) | 10 |
| 1.3. | Non-radiation + FPS (post radiation schedule) | 10 |
| 2.1. | 30Gy + saline (before radiation) | 10 |
| 2.2. | 30Gy + saline (post radiation) | 10 |
| 3.1. | 30Gy + carrier (albumin solution, before radiation schedule) | 10 |
| 3.2. | 30Gy + carrier (albumin solution, post radiation schedule) | 10 |
| 4.1. | 30Gy + FPS (before radiation) | 10 |
| 4.2. | 30Gy + FPS (post radiation) | 10 |

The FPS has been shown in previous experiments to cause no adverse effects on the rats. The albumin-solution carrier groups have results similar to the saline groups, all of which are irradiated. Any distress will come as a result of the exposure to radiation. Changes in body weight, coat condition and grooming behavior, eye and nasal discharge, dehydration, body position and movement, head tilt and circling behavior will all be used to monitor pain or distress in the animals.

A staff veterinarian is available to provide professional health care at all times. Routine physical observation and weighing will be made to the animals weekly. Listed criteria will be used to monitor and pain and stress. A) Weight loss greater than 15% within 2 weeks. B) Acute to chronic unresolved diarrhea. C) Acute to chronic unresolved infection. D) Acute unresolved respiratory distress. E) Behavioral Observation. F) Unconscious or poorly responsive to stimuli. G) Severe weakness. H) Abnormal neurological signs such as ataxia, head tilt, circling. I) Seizures. J) Abnormal hunched posture or unwillingness to move unresolved by analgesia. K) Inability to eat or drink. L) Poor grooming behavior, e.g. abnormal vocalizations. M) Abnormal increase in aggressive behavior upon handling. N) Anorexia. All aspects of the program for procurement, housing, management, veterinary care and disposal of carcasses follow the guidelines in the NIH Guide for the Care and Use of Laboratory Animals.

Description of irradiation procedures: The beam will be directed vertically downward, to project a 30×30 cm field at isocenter 80 cm source-to-axis distance with a build-up layer of 5 mm. The dose will be delivered in a single fraction at of 30 Gy to one hind leg. Dose calibration will be performed using a Capintec PR-06G cylindrical ion chamber (SN=5965) calibrated at an Accredited Dosimetry Calibration Laboratory which will confirm the delivered doses.

The data will show that the ulceration model is easy to use and that Fibrinoplate-S (FPS) is effective for the augmentation of stem cell function leading to effective treatment of Radiation-induced Skin Damage (the burn model). The data reveal that FPS is an effective prophylactic as well as therapeutic radioprotectant for use in radiation therapy. It is also important for those who are at risk of a substantial environmental exposure to radiation and any patient in need to better or faster stem cell function.

Material and Methods:

A total dose of 25 Gy was delivered to a hind leg of Sprague Dawley rats with co-balt-60 gamma radiation. (The planned administration of 30 Gy is not needed but is expected to lead to the same conclusions). The rats were treated with an infusion of 8 mg/kg of FPS intravenously or saline once a day for two days before or after irradiation. No rat died before day 51 from any cause. The rats were euthanized according to plan at day 51 following exposure. At the time of euthanasia, blood was obtained by cardiac puncture.

FPS was manufactured using the method disclosed in a patent titled "Mass Production of Ready-to-Use Suspensions of Fibrinogen-coated Albumin Spheres for treatment of Thrombocytopenic Patients" (Chinese Patent ZL 2013 1 0311735.1, issued in October, 2015; application also filed in the USPTO on Jul. 27, 2012, publication number 20140030347.)

The median diameter of the spheres is 0.15 microns, with no spheres larger than 1 micron in diameter. The concentration of fibrinogen as a fraction of the weight of sphere is 0.037 mg of fibrinogen per mg sphere. Control (blank) spheres of the same size distribution but without fibrinogen were also prepared, but not tested in this experiment.

Results:

No obvious toxicity was noted in the control and treatment groups. There was no significant difference in body weight between groups during the entire period of study. There was no significant difference in platelet counts and red blood cell counts among the different groups.

WBC (white blood cells) and particularly lymphocytes are sensitive to the lethal effects of irradiation. The concentration of WBC (and major leukocyte types) in the control-irradiated (IR) group is comparable to that of the control-non-irradiated group, showing that the irradiation to the hind leg is local and does not affect systemic concentration of blood cells.

The data showed radiation-induced effects and their modification by FPS: FIG. 1 shows that the sizes of skin lesion in FPS-treated groups were significantly smaller than non-treated controls (p<0.05), with FPS pre-IR means Fibrinoplate-S administered before irradiation, PS-post-IR means Fibrinoplate-S administered after irradiation, and Saline-IR means normal saline administered before and after irradiation.

The lesion sizes among post-treatment group (FPS administered post-irradiation) is smaller than those in the pre-treatment group (FPS administered before irradiation.) However, the difference is not statistically significant because only 4 animals were used per group.

Figure 2:
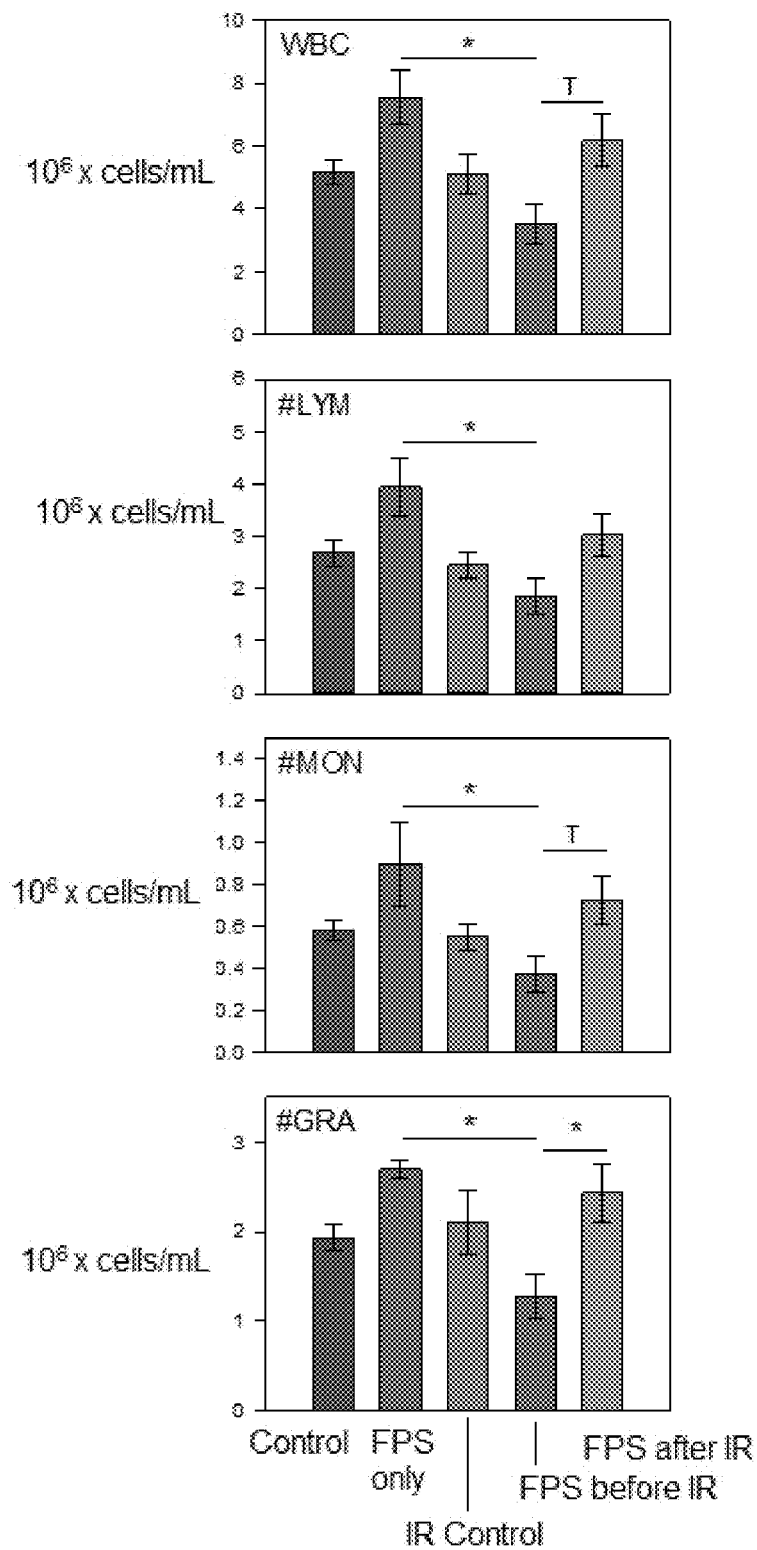
FIG. 2 is graphical views of the effect on radiation-sensitive blood cells.

FIG. 2 shows the effect on radiation-sensitive blood cells (WBC and its major subtypes) in sample of blood drawn about 51 days after the administration of (or lack of) FPS. The 1st and 2nd column from the left involve animals that have not been irradiated. With respect to the effect of FPS, the FPS-treated group (2nd column) shows a higher concentration of WBC (and the subgroups) than even the control group (non-irradiated, 1st column in FIG. 1). In fact, this FPS-treated (non-irradiated) group has the highest concentration of white blood cells (as well as all the major leukocyte types) compared to all the other groups (whether irradiated or not.) The data showed that two doses of FPS given about 51 days previously have a positive effect lasting at least 51 days. Because both FPS-treated and saline-treated groups did not get any irradiation, the effect is not due to irradiation. Also by 51 days there should not be much of any FPS left in the body, the difference between FPS-treatment and saline-treatment is likely due to an early effect by the FPS, possibly on the stimulation of stem cells, either by increasing the number of stem cells or by acceleration of their maturation, leading to a higher concentration of WBC (and its major subgroups) all in the setting of no irradiation.

The four panels in FIG. 2 show a similar trending of cell concentrations (collected on Day 51) towards the various treatments, whether it is the concentration of WBC, or lymphocytes (LYM), or monocytes (MON), or granulocytes (GRA). This suggests strongly that the common ancestor of all these mature blood cells has been affected and that it had responded differently to the different treatments (irradiated versus not irradiated, or by treatment of FPS versus albumin-solution treatment.) The data suggest strongly that the stem cells are affected, being augmented by the administration of FPS, both in the setting of no irradiation and in the setting of irradiation.

One mechanism to explain why the FPS-treated group (2nd column, no irradiation) has a higher concentration of WBC compared to the control (1st column, no irradiation) is the phenomenon of demargination. Demargination is the movement of cells (with no net increase in the total mass within the body) from where they normally reside (within the various tissues, e.g. the spleen) and entering into circulation within the vascular system (artificially inflating the concentration in the collected blood samples). However, because the blood is collect on day 51 with or without irradiation, by then the spheres should no longer be in the body to effectively "push" the WBC away from their normal places of hiding. The data suggest that the administration of FPS affects stem cell production, maturation or otherwise, leading to a higher concentration of WBC during this period of study. A higher WBC is beneficial because many patients suffering from low white cell counts will get infections.

FIG. 2 illustrates concentration of blood cells with and without irradiation (IR): WBC being white blood cells; #LYM being lymphocytes; #MON being monocytes; and #GRA being granulocytes.

The next three columns (the $3^{rd}$, $4^{th}$ and $5^{th}$ column from the left) in FIG. 2 show the effect of (a) no FPS treatment, (b) FPS pre-treatment, administered before irradiation (IR), (c) FPS post-treatment, administered after irradiation. The concentration of WBC and major leukocyte types in the FPS-post irradiation group is higher than that of the control (irradiated) group. In fact the FPS-pre-treatment group is worse than the control group. In fact, the pre-treatment group has cell concentrations that are the lowest among all groups.

One explanation can be the following. (a) In the pre-treatment group, FPS stimulates the conversion of stem cells to mature cells which are sensitive to radiation. The conversion depletes the finite store of competent stem cells. The mature cells (WBC and the subgroups) are then killed by the irradiation. Alternatively, the stem cells may have been killed directly. Although the irradiation is aimed locally at the leg, the leg bones are penetrated. This study is not aimed at studying how a "local" beam may affect the overall well being of WBC in the body. However, the overall store of competent stem cells is likely reduced and this event is reflected about 51 days later in the lowest concentration of WBC and the subgroups in this group among all treatment groups. (b) In the control group, there is no stimulation of the stem cells due to FPS administration (because the group is treated with a carrier fluid.) Therefore, the concentration of WBC is higher than even the pre-treatment group. (c) In the post-treatment group, the stem cells are stimulated only after any potential damage (by irradiation) is gone. Therefore, the post-treatment group has the highest WBC concentration among the 3 irradiated groups.

The data suggests that although FPS is inert in vitro and not known to affect cell concentrations with respect to mature blood cells (red cells, white cells and platelets) FPS may have a definitive effect on immature blood cells including stem cells.

The body's response on day 51 in terms of the different WBC and major leukocyte type concentration to the various treatment about 51 days before, is consistent with the previously disclosed data about reactive oxygen species (ROS) from spleen cells: in that a difference in activity can be observed even 51 days after irradiation among animals that received FPS compared to control animals that did not receive FPS (both groups exposed to irradiation.)

Figure 3:
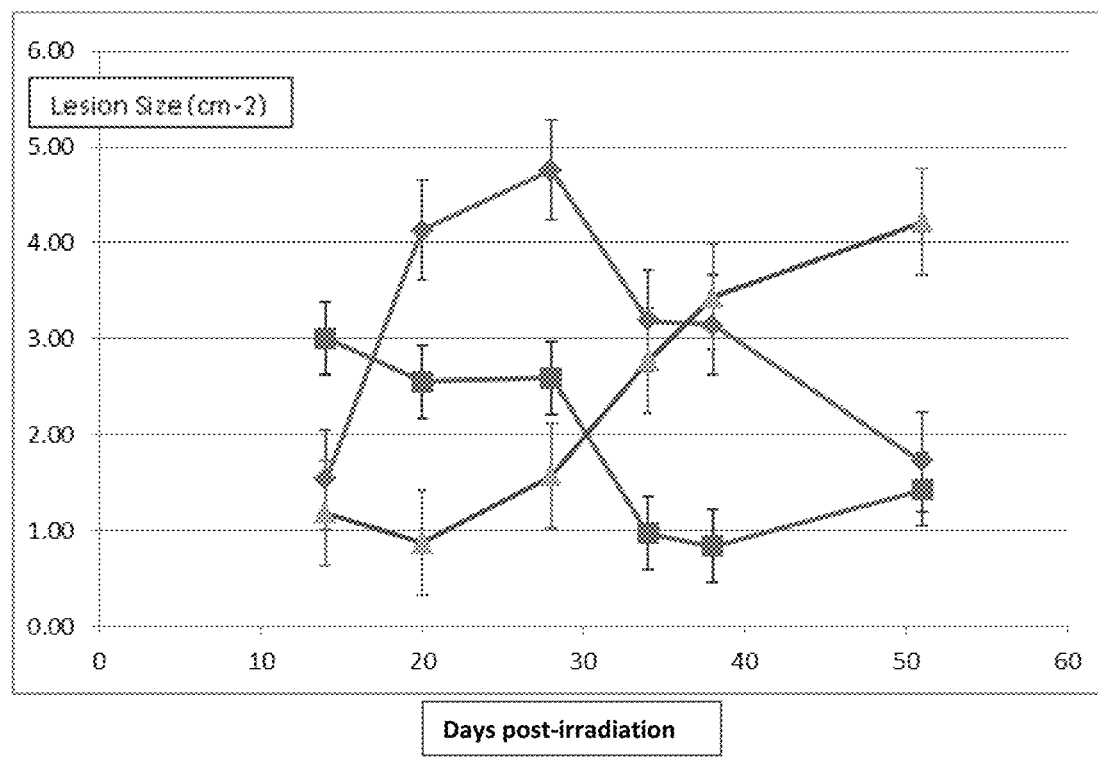
FIG. 3 is a graphical view of the progression of lesion sizes with the various treatments.

FIG. 3 shows the progression of lesion sizes with the various treatments. It should be noted that the lesion on day 51 in the control group has not reached maximum size yet, when the rats were sacrificed according to the protocol. In contrast, the peak lesion size for the pre-treatment group is reached on day 30 and has almost been reduced to its minimal size by day 51. Most interestingly, the post-treatment group lesion size has reached its peak size by the first time it was measured, which was day 14 post-irradiation and its lesion size has been reducing since that day. The appearance and development of lesion is the slowest in the control group which suggests that it is the body's delayed reaction to the irradiation event that brings about the skin ulceration. The data further shows that administration of FAS has a positive effect in (a) reducing the body's reaction to the insult, or (b) promoting faster healing. It is intended to further study the mechanisms of the development of the lesions and their healing processes.

FIG. 3 illustrates progression of Lesion Size (cm-2) with time (days after irradiation): Control (green triangles); Pre-treatment (blue diamonds); and Post-treatment (red squares) group.

Discussion

There are many advantages to the administration of FPS to augment stem cell function. (a) there are no observed side effects. (b) the treatment is effective whether given prophylactically or after the damage is done. (c) The post-treatment is better than the pre-treatment. However, due to the small number of animals used, the difference between treatment pre-irradiation versus post-irradiation is not statistically significant. The present invention expects to show a statistically significant different when a large number of animals are used.

The radiation-induced burn model is also a good model. The time needed to irradiate the animal is very quick, typically a few minutes with the animal experiencing minimal distress. The development of the ulcer is over a few days and can be observed and measured accurately as it progresses, before the whole ulceration cycle is completed. The animal experiences minimum pain, in contrast to thermal burns. If necessary, the other leg can be protected from irradiation and serve as a control area within the same animal. The animal will not die from the irradiation. There is no need to add antibiotics or pain medication during the process so there less potential interference from concomitant medical treatment.

Although the ulceration is induced with irradiation in this experiment, we believe that severe-cold temperature, such as by contact with a block of dry ice can induce similar burn reaction from the host, after which various burn-treatments can be evaluated.

Although the experiment is designed to test the healing process brought on by a burn-treatment modality, the same model can be useful to evaluate whether platelet transfusions can be equally effective. Platelet transfusions are not known to stimulate stem cell maturation or production. The efficacy of platelets that can be studied can include those that have been subjected to prior modifications, such as removal of certain platelet antigen, viral-inactivation processes, bacterial-decontamination procedures and any other method that is designed to improve the safety of donor platelets. Should other artificial platelet products other than the nanoparticles of the present invention become available, they can be tested on the present radiation-induced burn model also. This burn-model is easier to perform and less technician-skill-dependent than the performance of bleeding time. Should other medication become available that is useful to treat burn patients, which does not belong to the class of platelets or platelet substitutes, they can also be tested on this burn-model.

The present invention expects the blank spheres to show some improvement (smaller in size) in the size of the ulcer compared to the control group, because blank spheres have been shown to absorb and bind the host's coagulation factors in vivo. However, it is not expected that the effect to be as robust as treatment with FPS (which has fibrinogen added at the manufacturing process, guaranteeing at least a concentration of 0.037 mg fibrinogen per mg sphere before the spheres enter into the blood stream of the patient). Further experiments will delineate if a higher concentration (higher than 0.037 mg fibrinogen per mg spheres) added at the manufacturing step will have even better results.

Although the model here uses rats, any other suitable animals can be used, e.g. pigs, rabbits, or even non-human primates.

Conclusion:

This study showed that (a) FAS can possibly stimulate the production or maturation of stem cells, in general, promote augmentation of stem cell functions, in the non-irradiated animals as well as the irradiated animals; (b) although the present invention only measured WBC and the major subgroups or subtypes of blood cells in this experiment, other stem cells (leading to fibroblasts and other cells of regeneration) must also be involved because the lesion in the post-treatment group heals so much faster than the control group; (c) the model causes no great distress to the animals and is easy for use to quantify the effectiveness of agents that promotes stem cell augmentation. Even by using only 4 animals, it can be shown that the control group has lesion sizes almost three times larger than those in the treatment groups.

Comments:

In this model, the decrease in the size of the lesion was measured as an index of healing. There are many tissues involved in the healing process: skin, hair, glands, fat, muscle, nerves, and blood vessels. Therefore, the mechanism of action of the albumin nanospheres cannot be just the expected augmentation of the hemostatic function of the residual concentration of platelets in the host (as an artificial platelet), as described in the prior arts from Dr. Yen, e.g. "Biologic Devices for Hemostasis" issued on Aug. 25, 2015 (U.S. Pat. No. 9,114,127 B2). Indeed the animals in this experiment are not even thrombocytopenic—they have normal platelet counts and functions (non-thrombocytopenic.)

It is now known that stem cells can be isolated from a number of tissues, not just the bone marrow, but including fat, various other organs and from the endothelium. For example, the stem cells that form bone material during the healing of bone fractures can come, at least some of them, from the endothelium. According to Aaron Nauth and Emil H Schemitsch, "Stem Cells for the Repair and Regeneration of Bone" published in Indian J Orthop. 2012 January-February; 46(1): 19-21: "Our research group and others have recently reported on the use of a novel stem cell type for enhancing fracture healing, called endothelial progenitor cells (EPCs). EPCs represent a progenitor cell population of hematopoietic origin, with known ability to participate in angiogenesis. It has been shown that EPCs home to sites of tissue ischemia, affect functional blood flow recovery in ischemic tissues, and enter the circulating system in response to trauma."

The possibility that progenitor cells of any kind or any source, or stem cells from any number of sites can be "enhanced" or "augmented" can be good news for many patients who can benefit from the enhancement. In the normal person, there is always the "battle" between the destructive processes and the healing processes. If the healing process "wins" (through perhaps the cytokines and other factors) then after the period of sickness, the patient eventually will recover, whether the recovery is 100% back to normal or not. If however, at any time the disease process or the destructive forces "wins" the patient will "turn for the worse." At any time there may be progenitor cells in all the damaged tissues trying to catch up with the healing process but there are not enough of these "good cells" or they are not maturing fast enough. Therefore, having more of these cells produced, mobilized to the wounded site, or maturing faster and in greater numbers, can be a great medical benefit. These conditions would include: damage to any major organs or large amounts of tissues, traumatic situations like crushing of bones leading to gaps where the bones cannot join up, or misaligned and non-union of the bone pieces. Sometimes the surgeons would try to use bone implants to fill the missing volume but they do not always work. The result may be the amputation of a limb. Other conditions would include spinal cord injuries leading to nerve damage, or even Alzheimer's disease.

It can also be readily appreciated that the augmentation of stem cells can lead to faster recovery of the patient after "artificial injuries" such as surgeries. By necessity, surgeries would be trauma under controlled conditions where the unwanted tissues are removed or injuries caused by accidents are patched up. If every surgical patient can heal faster after the surgery, the economic impact will be tremendous.

Experiment Two

Optimization of the Fibrinogen Content Per Sphere

Purpose:

To evaluate if a certain concentration of fibrinogen per sphere can have optimal effect on the healing process and the rate of stem cells production Material and Method:

FPS was manufactured using the method as described in Experiment One. The median diameter of the spheres is 0.15 microns, with no spheres larger than 1 micron in diameter. As described, one volume of fibrinogen solution was added to three volumes of the blank sphere suspension at least two hours after appearance of turbidity.

Instead of using one concentration of fibrinogen, five concentrations of fibrinogen was used (all dissolved in a solution containing 1.5 mg sodium lauryl sulfate per ml of solution.) The concentrations were: (a) 0, (b) 0.5, (c) 1.0, (d) 1.3, (e) 2.0 mg dissolved fibrinogen per ml of solution.

Results:

The data show that the size of the lesion in rats (4 rats per group) were larger in (a), (b), (c) groups compared to (d) and (e). It shows that the optimal healing is accomplished by having spheres that have been manufactured by mixing one volume of fibrinogen solution containing 1.3 to 2.0 mg of fibrinogen per ml, with three volume of blank sphere suspension.

The size of the lesion in (e) appears to be 20% small than that of (d), however, due to the small number of animals used per group, the difference is not statistically significant. Further experimentation is needed to resolve whether fibrinogen solution (e) can result in spheres that will produce faster and more complete healing of radiation-induced skin ulcer than solution (d).

Experiment Three

Optimization of the Injection Protocol in the Model

Purpose:

To find out if a single dose or multiple-doses is superior to the two-dose regiment used in Experiment One; and if a different injection schedule offers even more improved results Design of the Experiment:

Since the full manifestation of skin ulceration may take many days to show up, the following protocol is designed to evaluate if there is an optimal dose-timing-schedule.

1. Single doses: (administered 24 hours after irradiation)
   a. at 8 mg spheres/kg
   b. at 16 mg spheres/kg
   c. at greater than 16 mg spheres/kg, e.g. 24 mg spheres/kg
2. Once the optimal medicine-dose is determined from single dose as above, the optimal time of administration of the single dose will be evaluated. Using the optimal dose from 1. (e.g. 16 mg sphere/kg, given on day 1 after irradiation) the following will be done.
   a. 16 mg sphere/kg, given in one dose on day 2 post-irradiation
   b. 16 mg sphere/kg, given in one dose on day 4 post-irradiation
   c. 16 mg sphere/kg, given in one dose on a day after day 4-post-irradiation
3. Once the optimal medicine-dose (e.g. 16 mg sphere/kg) and the optimal starting time (e.g. the best result is obtained with day 6 being the best day post-irradiation to give the single dose) is determined, the following will be done (two doses).
   a. 16 mg sphere/kg, given two times, on day 6 and 8 post-irradiation
   b. 16 mg sphere/kg, given two times, on day 6 and 10 post-irradiation
   c. 16 mg sphere/kg, given two times, on day 6 and after day 10 post-irradiation
4. Once the optimal medicine-dose (e.g. 16 mg sphere/kg) and the optimal starting time (e.g. start on day 6 post-irradiation) and the in-between time is decided (e.g. best interval time is 4 days, i.e. two doses, to be given on day 6 and day 10 post-irradiation) then the following will be done (effect of 3 doses).
   a. 16 mg sphere/kg, given three times, on day 6, 10 and 14 post-irradiation
   b. 16 mg sphere/kg, given three times, on day 6, 10 and after day 14 post-irradiation.

It can be readily appreciated that a lot of work will need to be done. However, the time needed to irradiate the rats is short and only 10 or fewer animals are needed to show a statistically significant difference between various treatment schemes. The data will be very helpful to the evaluation of other treatment methods in that the model will have been optimized to find the slightest differences between any two treatment methods.

Results:

The present invention expects that the best result will be obtained with the regiment of: 16 mg sphere/kg, given three times, on day 6, 10 and 14 post-irradiation. By best result it is meant that the largest difference between the burn-treatment group versus the control-placebo group, both of which are administered to irradiated animals to produce a radiation ulcer. The same regiment will also bring out the most sensitive response to any treatment method, thus allowing even slight improvements in the treatment method to be revealed. It is also expected that a higher dose of irradiation or a lower dose of irradiation, in combination of the treatment regiments presented above, may result in even better discrimination of effective treatment methods over less effective treatment methods.

The present invention also expects the best treatment modality revealed in this radiation-ulcer model to be the best treatment modality or regiment in both the laboratory setting as well as clinical setting, for the thermal burn patients, resulting in less need for transfusion products (e.g. fewer units of platelets, red cells etc.), faster recovery time, and lower mortality.

Experiment Four

Measuring Stem Cell Concentrations In Vivo in a Non-Human Primate Model

Purpose:

To evaluate if the healing process (which involves multiple tissue types, including skin, subcutaneous tissues, fibrioblasts, nerve cells, muscles, fat cells and non-cellular connective tissues) can be correlated to the stem cell concentration found in blood of the healing animal.

Material and Method:

Spheres prepared with a fibrinogen solution containing 1.3 mg fibrinogen per ml in manufacturing the spheres were used for this experiment. A package for taking images of the wound healing called SilhouetteConnect and SilhouetteStar will be purchased from Aranz Medical Limited located in Christchurch, New Zealand.

Experimental Designs:

The Objectives are:
1) To test the efficacy of two doses of Fibrinoplate-S (FPS, 16 mg spheres/kg intravenously), a suspension containing nanometer-sized fibrinogen-coated albumin spheres, administered intravenously to nonhuman primates 24 and 48 hours after induction of a radiation-induced skin ulcer on healing of skin ulcer
   a. Wound size determined digitally by laser, on days 1, 2, 3, 8, 15, 22, 30, 60
   b. Wound care provided daily or as needed
   c. Biopsy demonstration of wound endothelial, fibrosis, and inflammatory cell content to quantify contributions of angiogenesis, scar formation, and ongoing inflammation to wound size
2) To test the effect of FPS on hematopoietic parameters following localized radiation as measured by CBC (Days pre-radiation×2, 3, 8, 15, 22, 30, 50, 60=9 timepoints) and on blood chemistries (Kidney and liver function, days pre, 3, 30, 60)
3) To test the effect of FPS on endothelium and their stem cells;
   a. wound by microscopy to detect endothelial content
   b. bone marrow by flow cytometry to detect live stem cell (CD34+) and endothelial progenitor cells (CD31+ CD34+CD105+CD45−) ((pre×2, day 3, day 30, day 60)
   c. circulating endothelial progenitors by flow cytometry (pre×2, day 3, day 30, day 60) to quantify contribution of bone marrow derived endothelial progenitor cells on wound healing
4) To test the effect of FPS on immune host defense
   a. Determine bacterial content of wound-define type of bacteria and change of bacteria over time
   b. Measure toll like receptors in the wound and their mediators-presence of bacteria is required for healing, however persistence of bacteria along with persistent increase in inflammatory macrophages can perpetuate a chronic inflammatory state which is associated with delayed healing-Wound biopsies at baseline, and days 3, 30 and 60 will be taken to define inflammatory state of wound to determine of one mechanism of action involves reduction of inflammation.

TABLE 2

Schedule of Events

| Timepoint | FPS | CBC | CHEM | STEM CELL EVALUATION | ENDOTHELIUM | TLR | WOUND CULTURE | WOUND PHOTO |
|---|---|---|---|---|---|---|---|---|
| Pre-radiation 1 | | x | x | x | x | x | X with biopsy | |
| Pre-radiation 2 | | x | x | x | x | x | | |
| Day 1 | x | | | | | | | x |
| Day 2 | x | | | | | | | x |
| Day 3 | | x | x | x | x | x | X with biopsy | x |
| Day 8 | | x | | x | | | | x |
| Day 15 | | x | x | x | x | x | x | x |
| Day 22 | | x | | x | | | | x |
| Day 30 | | x | x | x | x | x | X with biopsy | x |
| Day 50 | | x | | x | | | | |
| Day 60 | | x | x | x | x | x | X with biopsy | x |

Test Subject and Design:

Six rhesus monkeys are available for placement of radiation burn wound on the deltoid area: 2 for control (saline solution 2 ml per kg); 2 for the FPS dose of 8 mg spheres/kg; 2 for the FPS dose of 16 mg spheres/kg.

Due to the nature of the analyses required per animal and at necropsy, it is planned to irradiate 2 animals in the first radiation session (cohort 1:1 control and one FPS, cohort 2:1 controls, 3 FPS). Radiation can be either from a superficial skin irradiator (operates in 30-120 kV photon energy, dose rate 240 cGy/min) or LINAC (which operates via 6 meV electron energy, 1 Gy/minute or lower). The superficial irradiator which is designed for skin will be calibrated prior to use for this work. Alternatively, the LINAC can be used but is higher energy typically used for total body irradiation with greater depth of field exposure.

Period of Performance will be approximately 4 months. A plexiglass container will be used for limb exposure. Wound measurements will be digitally recorded by the silhouette system (as described below).

Other points of care: items to be used for the care of the animal will include items such as alcohol pads, betadine pads, betadine solution, betadine spray, EDTA blood tubes, exam gloves, fentanyl patches for pain control, gauze pads for wound care, formalin for tissue biopsies, ketamine for sedation, masks, nanodots to measure radiation exposure, needles, syringes, vacutainer needles, antibodies for the detection of endothelial cells, stem cells, primers for toll like receptor analysis, silhouette wound software system, wound biopsy needles, plexiglass immobilizer for limb radiation exposure Results:

Final results and pathology studies are pending. However, preliminary results show that there is a noticeable increase in stem cell concentrations in vivo throughout the entire course of 60 days of observation in the non-human primates treated with FPS (whether the dose of FPS was 16 mg per kg or 8 mg per kg weight of the animal) as compared to the control. The size of the lesions were also smaller in the FPS-treated animals compared to the two control animals which were treated with saline on day 1 and day 2 post-irradiation. Due to the small number of animals used in this pilot study per group, it is possible that, but we cannot determine that the dose of 16 mg sphere/kg is statistically significantly better than the dose of 8 mg spheres/kg.

Conclusion:

The data showed that the administration of FPS at a dose of 8 mg/kg and 16 mg/kg given intravenously on day one and day two before or after irradiation will increase the concentration of stem cells leading to faster healing and a more complete resolution of the skin ulcer induced by irradiation, including all the tissues involved in regeneration of the area/volume previously affected by the irradiation. The present invention expects that a dose of 24 mg/kg may be equally effective, if not better than the comparatively lower doses. This finding suggests that the administration of FPS may benefit patients suffering from other diseases, trauma, events, old age, mental conditions (including Alzheimer disease) that can be helped by increased concentrations of the patient's own stem cells in vivo.

Other Conditions that can Benefit from the Present Invention

There are many conditions that can benefit from the present invention:

1. Conditions related to aging, particularly neurological conditions such as Senior Dementia or Alzheimer's disease.
2. Conditions related to a disease state which may or may not be directly related to aging or genetics, but can be aggregated by the accumulative effect of "unhealthy life style" e.g. heart disease.
3. Conditions related to trauma, e.g. car accidents, crush injuries to organs and bones, penetrating trauma, gun-shot wounds
4. Conditions related to artificial-trauma, e.g. surgery.
5. Other debilitating conditions include and not limited to diabetes, spinal cord injury, retinal disease, Parkinson's disease, heart disease and cancer.

In heart disease, work in mice has revealed that adult stem cells derived from non-heart tissues can repair the damaged heart by transforming into heart muscles. Such (small scale and routine) repair work may be going on at all times in the animal before the injury, but the trauma to the heart is too much for the body to respond adequately and so the animal dies. It may be possible that in small injuries to the heart, the mobilization of stem cells or precursor cells already in the body by the administration of the present invention can reverse the degradative processes in the animal caused by the trauma.

In stem cell research related to diabetes, it was found that some stem cells can be guided in the laboratory to produce specialized cells capable of producing insulin. It may be possible to induce certain stem cells already in the body by the present invention to become insulin-producing cells in vivo.

In Parkinson's disease research it was found that some transplanted stem cells can produce and release dopamine which can relieve the symptoms of Parkinson's disease. Much more needs to be worked on. But these preliminary data suggest that augmentation of the stem cells or precursor cells in vivo by the present invention may help the Parkinson patient.

Many people know that bone marrow transplant can benefit the cancer patient. However, there are many problems with transplanting stem cells from a donor. It may be possible to harvest the patient's own stem cells before the chemotherapy, reimplant them after the chemotherapy and use the present invention to rapidly increase the concentration or maturation the patient's own stem cells, thus reducing the vulnerable period of these patients during treatment.

Spinal Cord Injuries: in animal models, stem cell injections had positive effects on the motility of the animals after the otherwise-irreversible condition. The fact that in radiation-induced skin injury, the administration of the present invention 1 and 2 days after the injury is still effective (in fact more effective than administered pre-irradiation) offers much hope that the present invention can help patients when administered soon after the spinal cord injury.

Retinal Disease: Photoreceptor cells can be produced from stem cells and scientists have been able to transplant these cells to the retina. This should help patients with degenerative retinal diseases.

What is claimed as being new and desired to be protected by Letters Patent of the United States is as follows:

1. A method of increasing a concentration of white blood cells in a radiation-induced burn patient by augmenting a function of hematopoietic stem cells or precursor cells in vivo, said method comprising the steps of:
   a) preparing an albumin nanoparticle suspension containing albumin spheres, said albumin spheres being capable of augmenting a function or effectiveness of hematopoietic stem cells or precursor cells in vivo; and
   b) administering intravenously a dose of 16 mg/kg to 24 mg/kg of said albumin nanoparticle suspension to the patient;
   c) increasing the concentration of white blood cells in the patient by augmenting a function of the hematopoietic stem cells or precursor cells by said albumin spheres administered to the patient to repair cellular or tissue damage caused by radiation-induced burn;
   wherein said hematopoietic stem cells or precursor cells are mobilized from bone marrow by attaching said albumin spheres to endothelial cells inside the bone marrow;
   wherein the patient is non-thrombocytopenic.

2. The method according to claim 1 further comprising after step b), said albumin spheres administered to the patient decreasing extravasation of blood components from an intravascular compartment to an extravascular compartment, so that there is less free hemoglobin in the extravascular compartment.

3. The method according to claim 1 further comprising after step b) the step of stimulating a conversion of the stem cells or precursor cells to mature cells.

4. The method according to claim 1, wherein said albumin spheres of said albumin nanoparticle suspension are bound with fibrinogen molecules to produce fibrinogen coated albumin spheres.

5. The method according to claim 4, wherein said fibrinogen-coated albumin spheres are prepared using a fibrinogen solution containing 1.3 to 2.0 mg of fibrinogen per ml.

6. The method according to claim 4, wherein said fibrinogen molecules are bound to said albumin spheres in vitro.

7. The method according to claim 4, wherein said albumin nanoparticle suspension is comprised of said fibrinogen-coated albumin spheres, a supernatant, a first portion of a first desolvating agent, and a second portion of a second desolvating agent, where said albumin spheres do not sediment to form a layer within six months in said supernatant, said albumin spheres are always in contact with an aqueous phase medium since synthesis of said albumin spheres from soluble proteins and have not been exposed directly to air, where said supernatant comprises an excipient component including at least a sorbitol solution which renders said suspension compatible with blood in osmolarity and which is not degraded by heat treatment, and a sodium caprylate solution.

8. The method according to claim 7, wherein said first portion of said first desolvating agent is prepared to result in a concentration of said first desolvating agent insufficient to cause persistent turbidity of said suspension, and wherein said second portion of said second desolvating agent is prepared to result in a combined concentration of said first and second desolvating agent sufficient to cause formation of said albumin spheres stable against redissolving and without formation of aggregates.

* * * * *